United States Patent [19]

Baker et al.

[11] Patent Number: 5,766,927
[45] Date of Patent: Jun. 16, 1998

[54] INHIBITION OF PROTEIN DEGRADATION IN LIVING CELLS WITH DIPEPTIDES

[75] Inventors: Rohan T. Baker, Somerville; David K. Gonda, Quincy; Alexander Varshavsky, Boston, all of Mass.

[73] Assignee: Massachusetts Institute of Technology, Cambridge, Mass.

[21] Appl. No.: 230,453

[22] Filed: Apr. 20, 1994

Related U.S. Application Data

[60] Continuation of Ser. No. 936,019, Aug. 25, 1992, abandoned, which is a division of Ser. No. 373,825, Jun. 30, 1989, abandoned.

[51] Int. Cl.[6] .................... C12N 1/16; C12N 1/38; A61K 38/05; C12P 21/00
[52] U.S. Cl. .................. 435/255.1; 435/70.1; 435/71.1; 435/244; 435/325; 435/363; 435/366; 435/377; 514/2
[58] Field of Search .................. 435/69.1, 68.1, 435/69.2, 70.1, 70.2, 71.1, 244, 255.1, 325, 363, 366, 377; 514/2, 9

[56] References Cited

U.S. PATENT DOCUMENTS

| | | | |
|---|---|---|---|
| 4,512,979 | 4/1985 | Patchett et al. | 514/2 |
| 4,514,391 | 4/1985 | Gordon et al. | 514/2 |
| 4,551,445 | 11/1985 | Manning et al. | 514/9 |

FOREIGN PATENT DOCUMENTS

| | | |
|---|---|---|
| WO 88/02406 | 4/1988 | WIPO. |
| WO 89/09829 | 4/1989 | WIPO. |
| WO 89/12678 PCT/US | 6/1989 | WIPO. |
| 90/03669 | 6/1990 | WIPO. |

OTHER PUBLICATIONS

K. Nagai and H.C. Thogersen, *Nature* 309:810–812 (1984).
Hershko et al., *Proc. Natl. Acad. Sci. USA* 81:7021–7025 (1985).
Tsunasawa et al., *J. Biol. Chem.* 260:5382–5391 (1985).
Boissel et al., *Proc. Natl. Acad. Sci. USA* 82:8448–8452 (1985).
Thornton et al., *J. Mol. Biol.* 167:443–460 (1983).
Ferber et al., *J. Biol. Chem.* 261:3128–3134 (1986).
Bachmair et al., *Science* 234:179–186 (1986).
Ferber et al., *Nature* 326:808–811 (1988).
Reiss et al., *J. Biol. Chem.* 263:2693–2698 (1988).
Townsend et al., *J. Exp. Med.* 168:1211–1224 (1988).
Bachmair and Varshavsky, *Cell* 56:1019–1032 (1989).
Chau et al., *Science* 243:1576–1583 (1989).
Gonda et al., *J. Biol. Chem.* 264:16700–16712 (1989).
Miller et al., *Biotechnology* 1:698–704 (1989).
Kopitz et al., *Biochem. J.* 267:343–348 (1990).

*Primary Examiner*—David M. Naff
*Attorney, Agent, or Firm*—Kevin M. Farrell

[57] ABSTRACT

The half-life of a Type I, II and III non-compartmentalized intracellular proteins is increased in living eukaryotic cells by contacting the cells with a regulator having an amino-terminal amino acid residue which is the same or similar to the amino-terminal residue of the intracellular protein. The regulator is a dipeptide, a small polypeptide or a carboxyl-terminal derivative of an amino acid. The dipeptide or small polypeptide has an N-terminal amino acid residue which is Arg, Lys or His for the Type I protein, Phe, Leu, Trp, Tyr or Ile for the Type II protein and Ala, Ser or Thr for the Type III protein. The carboxyl-terminal derivative of an amino acid may be an amino acid modified at its C-terminus by the addition of a group selected from methyl, ethyl, propyl, butyl and isobutyl. The amino acid modified is the N-terminal amino acid residue of the dipeptide or small polypeptide for the respective Type I, II and III proteins. Compositions may be formed containing the regulator for contacting with the cells. Increasing the half-life of intracellular protein with the regulator may be used for treating diseases resulting from an abnormal breakdown of a desired protein, and for enhancing in vivo production of a desired protein.

6 Claims, 10 Drawing Sheets

5,766,927

1

INHIBITION OF PROTEIN DEGRADATION IN LIVING CELLS WITH DIPEPTIDES

This application is a continuation of application Ser. No. 07/936,019, filed Aug. 25, 1992, which is a Division of application Ser. No. 07/373,835, filed Jun. 30, 1989, both now abandoned.

GOVERNMENT SUPPORT

Work leading to this invention was supported by a grant from the National Institutes of Health.

BACKGROUND OF THE INVENTION

The half-lives of intracellular proteins range from a few seconds to many days. One major function of intracellular protein degradation is selective elimination of damaged or otherwise abnormal proteins. Another role of degradation pathways is to confer, either permanently or transiently, short half-lives on undamaged proteins whose intracellular concentrations must vary as a function of time. Many other proteins, while long-lived as components of larger macromolecular complexes, such as ribosomes or oligomeric proteins, are metabolically unstable in a free (unassociated) state.

Rates of selective protein degradation are a function of the cell's physiological state, and appear to be controlled differentially for individual proteins. Metabolic instability of normally short-lived proteins allows for rapid adjustment of their intracellular concentrations through regulated changes in rates of synthesis or degradation. The few instances in which the metabolic instability of an intracellular protein has been shown to be essential for its function include the cII protein of bacteriophage lambda and the HO endonuclease of the yeast *Saccharomyces cerevisiae*.

Most of the selective turnover of intracellular proteins under normal metabolic conditions is ATP-dependent and, in eukaryotes, nonlysosomal. Recent biochemical and genetic evidence indicates that, in eukaryotes, covalent conjugation of ubiquitin to short-lived intracellular proteins is essential for their selective degradation. The rules which determine whether a given protein is metabolically stable or unstable in-vivo were previously unknown.

Bachmair et al., *Science*, 234:179–186 (1986); *Cell*, 56:1019–1031 (1989) describe methods for generating desired amino-terminal residues in proteins and methods for influencing the metabolic stability of proteins using the N-end rule. Bachmair et al. discovered that the nature of the amino acid exposed at the amino terminus of an intracellular protein is a crucial determinant that specifies whether a protein will be metabolically stable or short-lived in vivo. Individual amino acids can be categorized as either stabilizing or destabilizing amino acids with respect to the degree of metabolic stability (half-life) that they confer upon a protein when exposed at the protein's amino terminus. Destabilizing amino acid residues confer short half-lives, which can be as short as a few minutes for some of the destabilizing amino acids. Stabilizing amino acid residues confer long half-lives, which can be many hours long. This dependency of a protein's half-life on the nature of its amino-terminal residue is referred to as the N-end rule. The degradative pathway whose initial steps involve the amino-terminal recognition of proteolytic substrates has been called the N-end rule pathway.

Since the discovery of the N-end rule of protein degradation by Bachmair et al., cited supra, its existence has been repeatedly confirmed both in further studies by the same group and by other investigators (Reiss et al., *J. Biol. Chem.* 263 (6), 2693–98 (1988)). For many applications, it would be extremely useful to specifically inhibit the N-end rule pathway-dependent protein degradation in living cells, because it would make it possible to influence or specifically perturb cellular processes such as cell proliferation and differentiation.

DISCLOSURE OF THE INVENTION

This invention pertains to a method of selectively inhibiting the degradation, in intact cells and whole animals (i.e., in vivo) of specific groups of proteins, as well as to compositions useful in the method. The present method, which is referred to as a method for inhibiting the N-end rule pathway in living cells, makes use of the knowledge that the nature of the amino acid present at the amino terminus of a protein is an important determinant of the half-life of that protein. Through use of the present method and compositions, it is possible to alter (extend) the half-lives of specific proteins or types of proteins and, as a result, to affect cellular processes in which these proteins are involved, such as cell proliferation and differentiation. In the present method, an agent referred to as a regulator is introduced into cells under appropriate conditions that allow it to bind to and inhibit a significant proportion of a specific N-end-recognizing protein factor, and, thereby, to inhibit a specific subset of the N-end rule pathway in-vivo. The specific subset is that portion of the N-end rule pathway that is governed by the N-end recognizing activity which is inhibited by the regulator. For example, a regulator having a basic amino-terminal residue will inhibit the basic N-end recognizing activity that forms a subset of the N-end rule pathway. As a result, intracellular proteins which have the same amino acid residue or a similar residue at their amino termini participate in the N-end rule pathway to a lesser extent than they would if the regulator were not present, and their respective in vivo half-lives are increased.

The regulator is an amino acid derivative, such as a dipeptide, a small polypeptide or another carboxyl-terminal derivative of an amino acid which is the same as or similar to the amino-terminal residue of the intracellular protein(s) whose metabolic stability is to be increased.

The nature of the amino acid residue present at the amino terminus of a protein is a determinant of the half-life of the protein. For example, in the yeast *S. cerevisiae*, the destabilizing class of amino-terminal residues includes such amino acids as isoleucine, glutamic acid, tyrosine, glutamine, phenylalanine, leucine, asparagine, aspartic acid, lysine, arginine, tryptophan and histidine. According to the same rule, the stabilizing class of amino-terminal residues includes such amino acids as methionine, serine, glycine, alanine, threonine, valine, cysteine and proline.

The method of the present invention can be used in all organisms that possess the N-end rule pathway. This is so because although the specific members of the two classes (stabilizing and destabilizing) of amino-terminal amino acid residues vary somewhat among different eukaryotes, a specific N-end rule applies in each case, and both destabilizing and stabilizing amino acids can readily be identified for a particular eukaryote. For example, in the recently determined N-end rule of mammalian reticulocytes (Gonda et al., *J. Biol. Chem.*, in press), cysteine, alanine, serine and threonine, which are stabilizing amino acids in yeast, have been shown to be destabilizing ones in reticulocytes. Conversely, isoleucine, which is destabilizing in yeast, is stabilizing in reticulocytes. In a similar manner to that described by Gonda et-al., cited supra, it is possible to ascertain the exact form of the N-end rule in any chosen cell or organism.

A regulator of the present invention includes an amino-terminal residue which, when present at the amino terminus of an intact intracellular protein, decreases the half-life of that protein in the cell. When used in the present method, however, the destabilizing amino-terminal residue present in a regulator, in fact, increases the half-life of the intracellular protein by acting as a "decoy" that competes with a short-lived intracellular protein for binding to an N-end-recognizing component of the N-end rule pathway. As a result, the otherwise short-lived protein is targeted less efficiently by the N-end rule pathway, and its half-life in the cell increases.

The compositions and methods of the present invention may be useful in treating diseases resulting from abnormal (e.g., excessive) in vivo degradation of particular proteins observed in a variety of catabolic states such as, for instance, in muscle wasting, or from insufficient levels of a normally short-lived protein whose artificial metabolic stabilization, through the present invention, may halt or reverse the disease. The method may also be used to increase yields in a biological production process over those which would result in the absence of the regulator (an inhibitor of the N-end rule pathway).

As a result of the present invention, it is possible, for the first time, to inhibit the N-end rule pathway in vivo (i.e., in intact cells, and whole animals). It is unexpected that a substance such as, for example, a leucine methyl ester, which is readily hydrolyzed in vivo into methanol and (inactive) free leucine, could accumulate in intact cells to a level sufficient for the effective inhibition of the N-end rule pathway. This, however, has now been shown to be the case. The present invention thus opens up a new way to selectively inhibit the degradation of specific proteins in intact cells and whole animals.

The bands are labeled as βgal (β-galactosidase), 90 kD (a discrete, metabolically stable cleavage product of βgal; note its absence from the lanes with metabolically stable Val-βgal), and X (an unrelated, endogenous yeast protein cross-reacting with the monoclonal antibody to βgal).

Figure 7:
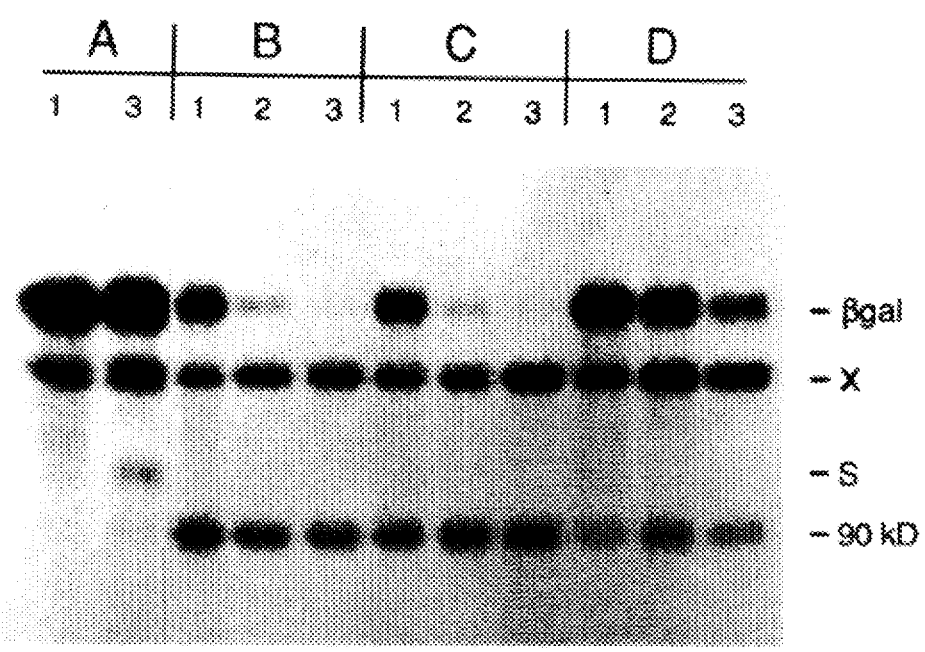

FIG. 7 is a photograph showing the stabilization of Leu-βgal in-vivo by L-Trp-L-Ala dipeptide, but not by L-Ala-L-Trp dipeptide. The photograph depicts the results of a pulse-chase experiment (5 minute pulse) with yeast cells expressing Val-βgal (A), Leu-βgal (B), Leu-βgal in the presence of 10 mM L-Ala-L-Trp (C), and Leu-βgal in the presence of 10 mM L-Trp-Ala (D). The cells were incubated with a dipeptide for 4 hours at 30° C.

The time points are 0 minutes for lane 1, 10 minutes for lane 2, and 30 minutes for lane 3. The labels for the bands are described above in the description of FIG. 5 with the addition of band "S", a βgal cleavage product specific for long-lived βgal species.

Figure 8:
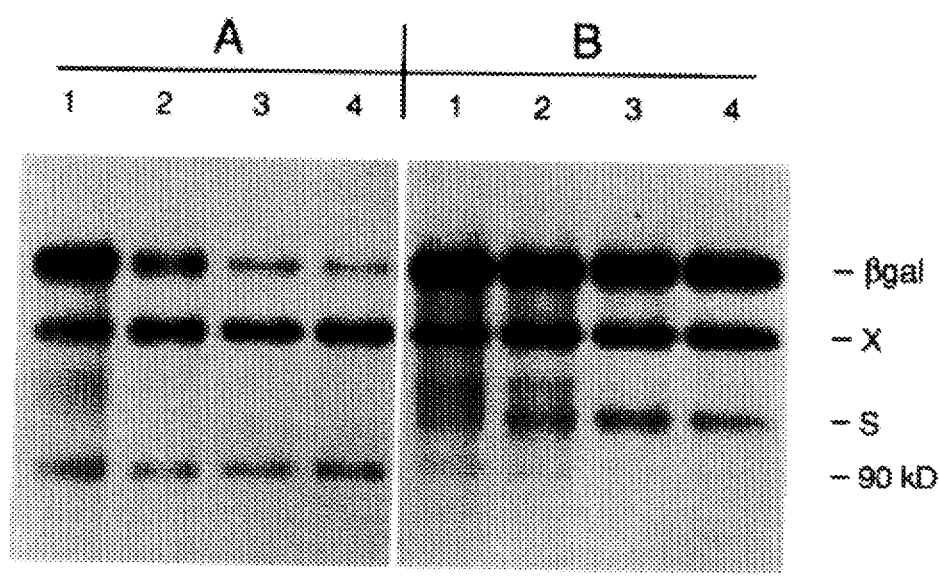

FIG. 8 is a photograph showing the in vivo metabolic stabilization of Tyr-βgal by Leu methyl ester. The photograph depicts the results of a pulse-chase experiment (3 minute pulse) with yeast cells expressing Tyr-βgal in the absence (A) or presence (B) of a 4 hour incubation with 10 mM Leu methyl ester. The time points are 0 minutes for lane 1, 10 minutes for lane 2, 30 minutes for lane 3, and 60 minutes for lane 4. Note the accumulation of a βgal breakdown product ("S") that is normally seen only with long-lived βgals. Note also the decrease in the amounts of the 90 kD cleavage product in the presence of Leu methyl ester.

Figure 9:
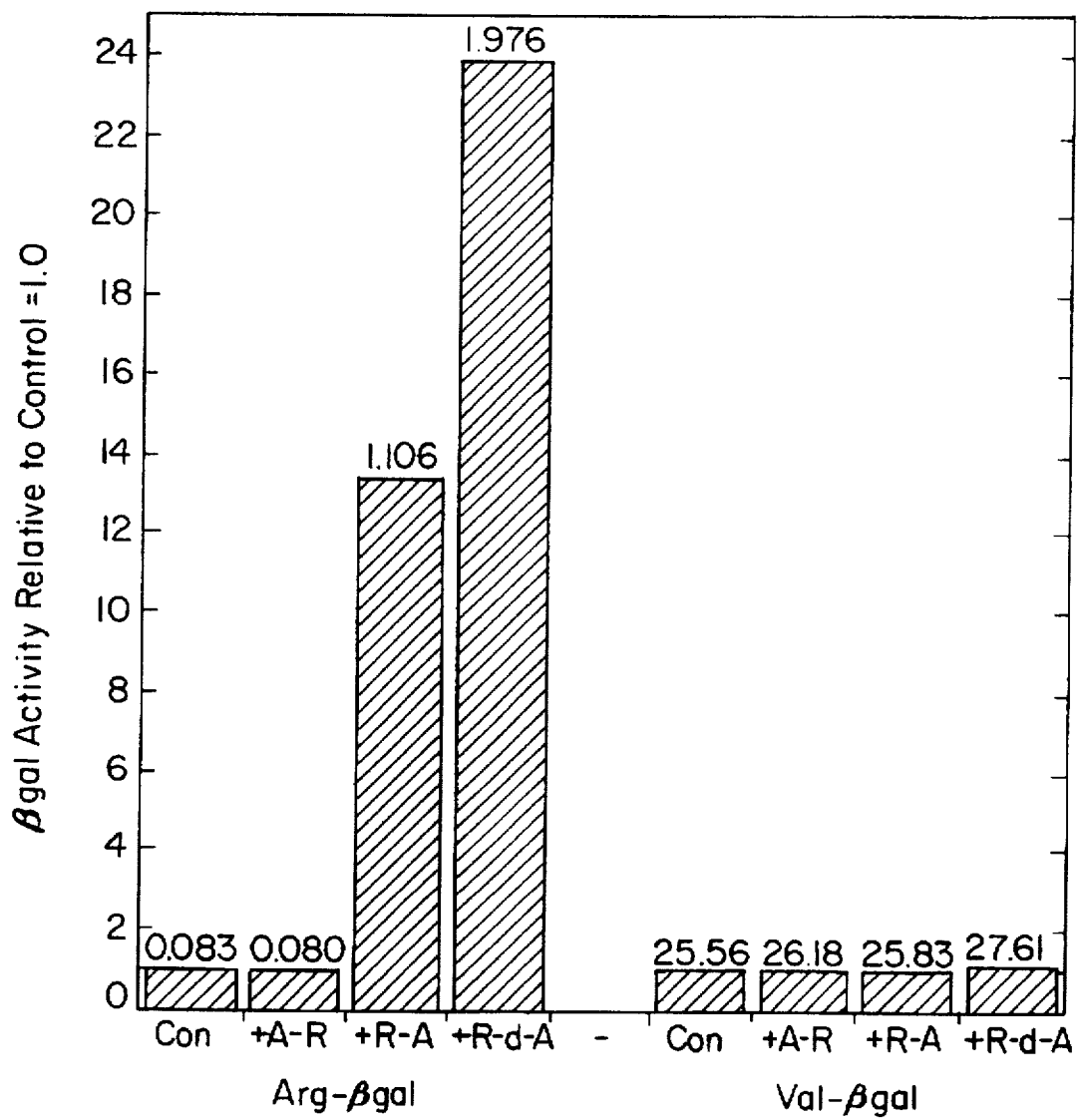

FIG. 9 is a bar graph demonstrating the effect of the stereoconfiguration of the amino acid residues in the Arg-Ala dipeptide on its ability to metabolically stabilize Arg-βgal. Yeast cells expressing Arg-βgal and Val-βgal were incubated for 2 hours in the presence of the indicated dipeptide (either L-Ala-L-Arg, L-Arg-L-Ala or L-Arg-D-Ala). βgal activity in the cells was then determined and plotted relative to the activity of an untreated control ("Con"). The actual βgal activity is given above each column. Stereoconfigurations of amino acid residues are of the "L" form unless otherwise noted.

DETAILED DESCRIPTION OF THE INVENTION

The present invention is based on the determination that degradation of specific types or classes of proteins can be inhibited (partially or completely) in living cells. According to the method of the present invention, inhibition of degradation of selected protein types or classes is carried out by incorporating or introducing into cells an agent, referred to as a regulator, which includes an amino acid which is the same as or similar to the amino-terminal amino acid of the protein(s) whose degradation is to be inhibited. The present invention further relates to the regulators themselves, which are amino acid derivatives, such as dipeptides, small polypeptides or other carboxyl-terminal derivative, in which the amino-terminal residue is the same as or similar to the amino-terminal residue of the cellular protein whose degradation is to be reduced (i.e., whose metabolic stability or half-life is to be increased). Carboxy terminal derivatives of the present invention have a free (unblocked) a-amino group on the amino N-terminal residue and a blocked or "substituted" carboxyl terminus (e.g., by another amino acid (to give a dipeptide or polypeptide) or by an alkylester).

The N-End Rule

As described in co-pending U.S. Ser. No. 07/103,910, filed Oct. 1, 1987, now abandoned, the N-end rule defines the criteria or the characteristics of an intracellular protein which determines the rapidity with which is it degraded by intracellular pathways. This rule and the N-end rule pathway are now summarized in the following paragraphs in order to provide background for the subsequent detailed explanation of the present invention. Study of the test protein, an enzyme β-galactosidase (βgal) was carried out, using various forms of the engineered protein in which a selected amino acid residue was present at the amino terminus of the processed protein, which was initially produced as a fusion protein with ubiquitin. When a chimeric gene encoding a ubiquitin-β-galactosidase fusion protein was expressed in the yeast S. cerevisiae, ubiquitin was shown to be cleaved from the nascent fusion protein, yielding a deubiquitinated β-galactosidase (βgal). This cleavage took place regardless of the nature of the βgal's amino acid residue, X, present at the ubiquitin-βgal junction. This result made it possible to expose any desired amino acid residue at the amino termini of otherwise identical X-βgal proteins. The X-βgal proteins so designed exhibited strikingly different half-lives in vivo (e.g., approximately 3 minutes to more than 20 hours). The half-life of a given X-βgal protein was shown to depend upon the nature of the amino acid residue X at the amino terminus of X-βgal.

As a result, it became possible to order the fundamental set of 20 amino acids according to the half-lives which they confer on βgal when exposed at its amino terminus. The resulting code or rule, referred to as the N-end rule, is shown in the Table.

THE N-END RULE in Yeast and Mammalian Reticulocytes

| | | Half-life of X-βgal | |
|---|---|---|---|
| | | yeast (in vivo) | reticulocytes (in vitro) |
| Primary destabilizing residue X | | | |
| Type I | Arg | 2 minutes | 1.0 hours |
| | Lys | 3 minutes | 1.3 hours |
| | His | 10 minutes | 3.5 hours |
| Type II | Phe | 3 minutes | 1.1 hours |
| | Leu | 3 minutes | 5.5 hours |
| | Trp | 3 minutes | 2.8 hours |
| | Tyr | 10 minutes | 2.8 hours |
| | Ile | 30 minutes | 20 hours |
| Type III | Ala | >20 hours | 4.4 hours |
| | Ser | >20 hours | 1.9 hours |
| | Thr | >20 hours | 7.2 hours |
| Secondary destabilizing residue X | | | |
| Asp | | 3 minutes | 1.1 hours |
| Glu | | 30 minutes | 1.0 hours |
| Cys | | >20 hours | 1.2 hours |
| Tertiary | | | |

THE N-END RULE in Yeast and Mammalian Reticulocytes

| | Half-life of X-βgal | |
|---|---|---|
| | yeast (in vivo) | reticulocytes (in vitro) |
| destabilizing residue X | | |
| Asn | 3 minutes | 1.4 hours |
| Gln | 10 minutes | 0.8 hours |
| Stabilizing residue X | | |
| Val | >20 hours | 100 hours |
| Met | >20 hours | 30 hours |
| Gly | >20 hours | 30 hours |
| Pro* | >20 hours | >20 hours |

*The rate of in vivo deubiquitination of Ub-Pro-βgal is low in both yeast and mammalian cells. The $t_{1/2}$ shown is that of the Pro-βgal protein.

As shown in the Table, the amino acids methionine, serine, alanine, threonine, valine, glycine and cysteine, when exposed at the amino terminus on X-βgal, confer on X-βgal half-lives of more than 20 hours in yeast. These are the most "stabilizing" of the amino acids. [Long half-lives of the X-βgal proteins which bear stabilizing amino-terminal residues can be considered a "default" consequence of the absence of E3 N-end-recognizing proteins specific for these residues]. Isoleucine and glutamic acid confer half-lives of approximately 30 minutes, and tyrosine, glutamine and histidine confer half-lives of approximately 10 minutes. Phenylalanine, leucine, aspartic acid, asparagine, and lysine, when present at the amino terminus of X-βgal, result in a half-life of approximately three minutes and arginine, the most destabilizing amino acid, confers a half-life of approximately two minutes.

Relatively long-lived ($t_{1/2}$>1 hour), noncompartmentalized intracellular proteins in both prokaryotes and eukaryotes have been shown to have amino-terminal residues of the stabilizing class, as predicted by the N-end rule. The same work demonstrated that although the presence of a destabilizing residue at the amino terminus of a protein is often sufficient for metabolic destabilization of the protein in vivo, this is not always the case. When such metabolic destabilization occurs to a relatively small extent, further analysis shows either an insufficient steric accessibility of the amino-terminal residue or a lack of the second determinant of the complete amino-terminal degradation signal. The second determinant of the amino-terminal degradation signal, which alone is also not sufficient to metabolically destabilize a protein, was found to be a specific internal lysine residue. The ability of this critical lysine residue to serve as the second determinant was shown to be largely independent of unique amino acid sequences surrounding the residue. Instead, the essential features of the critical lysine residue were shown to be its spatial proximity to the protein's amino terminus and high segmental mobility of the region containing the lysine residue. The mechanistic significance of the second determinant was illuminated by the finding that in a targeted, short-lived protein, a chain of branched ubiquitin-ubiquitin conjugates is confined to a lysine residue that has been identified in the above work as the second determinant of the degradation signal (Bachmair and Varshavsky, Cell 56:1019–1031 (1989); Chau et al., Science 243:1516–1583 (1989).

The N-End Rule Pathway

As described elsewhere, most nascent proteins appear to lack ubiquitin moieties. (Varshavsky, A. et al., "The N-End Rule of Selective Protein Turn-over", In: UBIQUITIN (M. Rechsteiner, ed.), Plenum Publishing Corp. (1988); Bachmair and Varshavsky, Cell 56:1019–1032 (1989)). The mature amino termini of nascent, noncompartmentalized proteins are generated in vivo through the action of proteases whose substrate specificities have been partially characterized. Of particular interest is the consistent absence of destabilizing residues from the mature amino termini of relatively long-lived, noncompartmentalized proteins. This is largely due to the substrate specificity of the enzyme methionine aminopeptidase. This enzyme has been shown to cleave off the amino-terminal methionine residue (a stabilizing residue according to the N-end rule) in a nascent protein if and only if it is not followed by a second methionine residue or by one of the 12 amino acid residues that are destabilizing, according to the N-end rule. The inverse correspondence between the N-end rule and the substrate specificity of methionine aminopeptidase provides a partial functional explanation for the properties of this enzyme: a methionine-clipping aminopeptidase that is involved in processing of long-lived proteins would be expected not to expose a residue whose presence at the amino terminus might metabolically destabilize the substrate protein.

It has been suggested that analogous proteases may be responsible for generating amino termini bearing destabilizing amino acid residues in certain proteins whose aminoterminal sequences contain sites recognized by such proteases. (Varshavsky, A. et al., "The N-End Rule of Selective Protein Turnover", In: UBIQUITIN (M. Rechsteiner, ed.), Plenum Publishing Corp. (1988)).

The previously offered biochemical and genetic evidence also suggests that the N-end-recognizing components of the N-end rule pathway have a direct and specific affinity for the amino-terminal destabilizing residues of substrate proteins. Subsequent steps in the degradation of a targeted protein involve assembly of a ubiquitin-protein ligase complex at the bound proteolytic substrate, ubiquitination of the substrate, and its degradation by a "downstream" enzyme for which the ubiquitin moieties serve as either recognition signals or denaturation devices or both. This degradative pathway, in which the initial steps involve amino-terminal recognition of proteolytic substrates, is called the N-end rule pathway.

Inhibition of the N-End Rule Pathway in Living Cells

It has now been determined, through the experiments described in this application, that it is possible to inhibit the N-end rule pathway in living cells and, as a result, to selectively inhibit the degradation in living cells of specific types or classes of short-lived proteins.

A common feature of the proteins whose in-vivo degradation can be inhibited by the present method is the presence of amino-terminal residues that are destabilizing according to the N-end rule. In the present method, an agent, referred to as a regulator, is introduced into cells in which inhibition of the N-end rule pathway, as it applies to a selected type or class of intracellular protein(s), is desired. The regulator used in the method is an amino acid derivative (e.g., a dipeptide, a small polypeptide, or another carboxyl-terminal amino acid derivative) in which the amino-terminal amino acid is the same as or of the same class as the amino-terminal amino acid residue of the protein(s) whose degradation via the N-end rule pathway is to be inhibited.

For example, in the case of inhibition of in vivo degradation (increased half-life) of an intra-cellular protein which has an amino-terminal leucine residue, an amino acid derivative (e.g., a methyl ester) which contains leucine (a bulky hydrophobic residue) as the amino-terminal residue can be introduced into cells in sufficient quantity to interfere with the N-end rule-mediated recognition of that protein as a proteolytic substrate. Alternatively, an amino acid derivative (e.g., a methyl ester or a dipeptide) which includes tryptophan (another bulky hydrophobic residue) can be used to inhibit degradation of the same protein. As described in Examples 5, 6 and 7, the half-life of leucine-βgal is extended in yeast cells in the presence of either leucine methyl ester (FIG. 6) or L-tryptophan-L-alanine dipeptide (FIG. 7).

The rule that governs the "similarity" of a given destabilizing amino acid to another destabilizing amino acid is provided by the Table.

Figure 2:
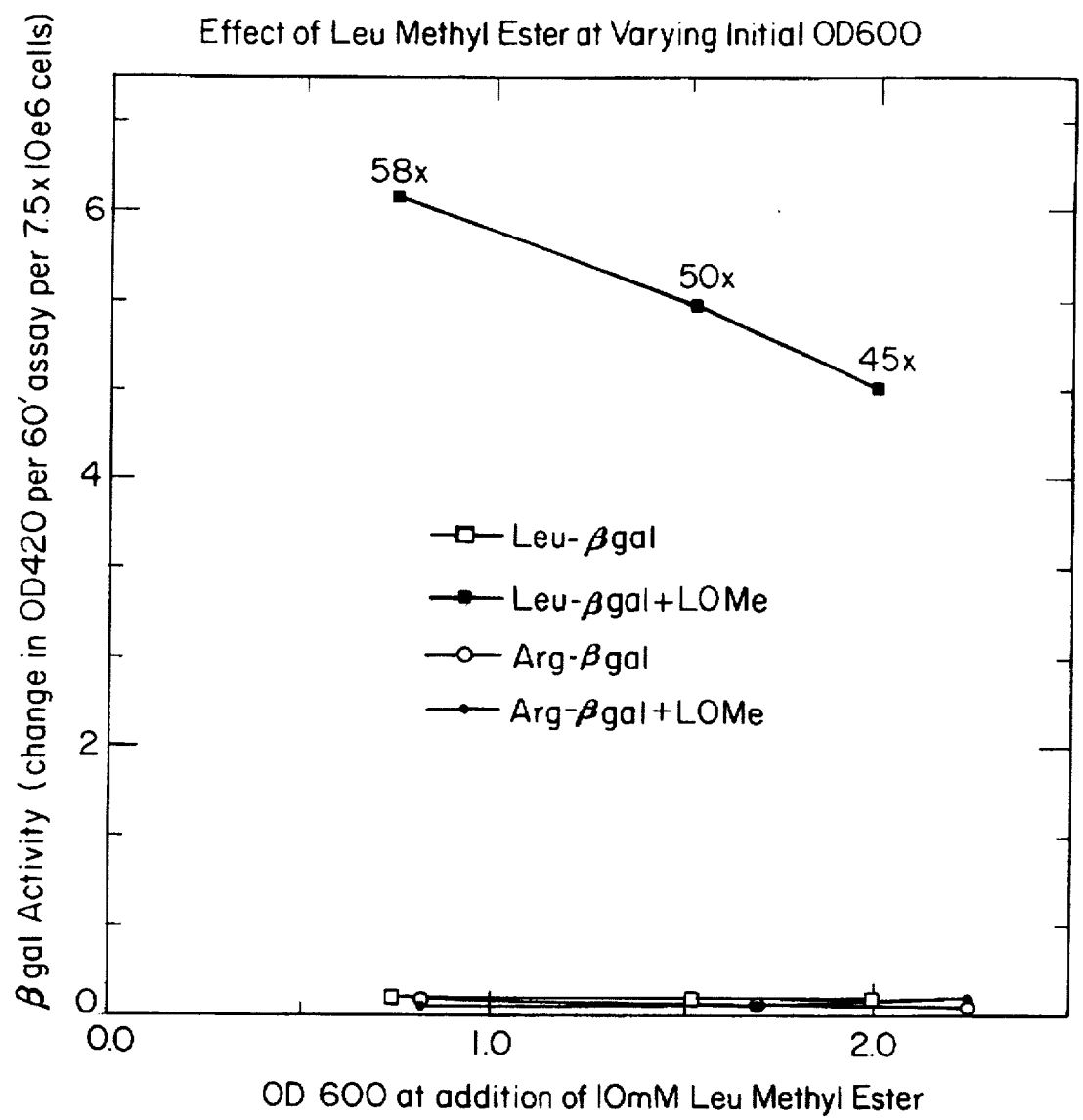
FIG. 2 is a graphic representation of the in vivo effect of Leu methyl ester at varying initial $OD_{600}$ cell density.

As shown in the Table, there are three experimentally distinguishable classes of N-end-recognizing activities in mammalian cells such as reticulocytces (Type I-III) and two classes of N-end-recognizing activities in yeast (Type I and II). Thus, a regulator whose destabilizing amino-terminal amino acid residue is of the same type (I, II or III; see the Table ) as a destabilizing amino-terminal residue in a target protein, will competitively inhibit the degradation of that protein in vivo, but will not inhibit the degradation of another substrate of the N-end rule pathway whose destabilizing amino-terminal residue belongs to a different type (FIGS. 2 and 5).

Stabilizing and destabilizing groups for each eukaryote can be determined as described by Bachmair et al., cited supra. Ubiquitin-X-βgal technology can be used to produce a set of proteins differing only in their amino-terminal residue, and then the identities of stabilizing and destabilizing residues can be determined by observing the rate of degradation of each X-βgal in the eukaryote of choice.

Figure 5A:
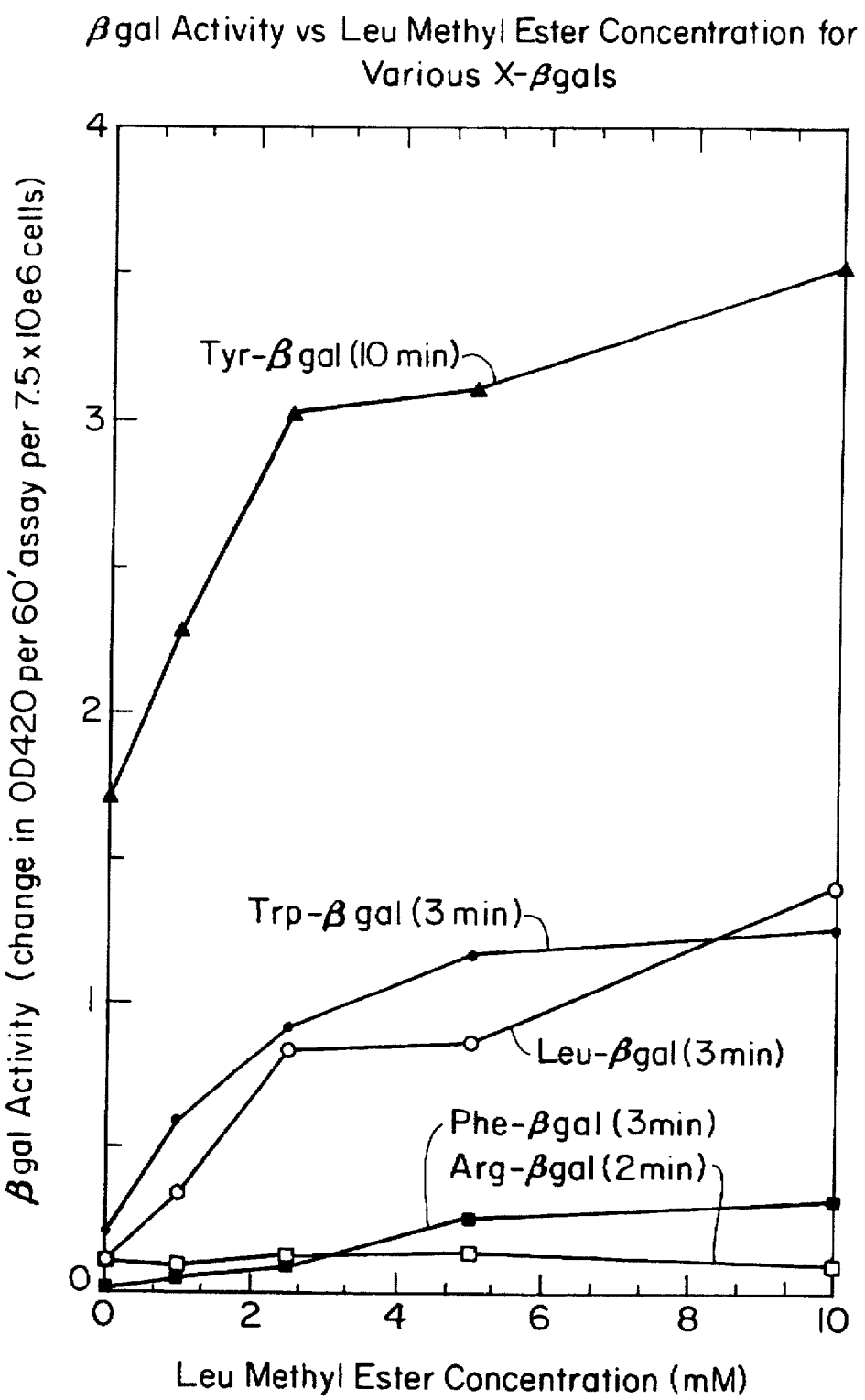
FIG. 5 is a graphic representation of the effect of Leu methyl ester on steady state levels of βgal proteins with bulky hydrophobic amino-terminal residues. Exponentially growing yeast cells harboring plasmids expressing Phe-βgal, Leu-βgal, Trp-βgal, Tyr-βgal, and Ile-βgal were supplemented with Leu methyl ester at concentrations ranging from 0 to 10 mM, incubated for 1 hour and assayed for the intracellular βgal activity. Half-lives of the X-βgal proteins (determined according to the methods of Bachmair et al., Science, 234:179 (1986)) are given in parentheses.
Figure 5B:
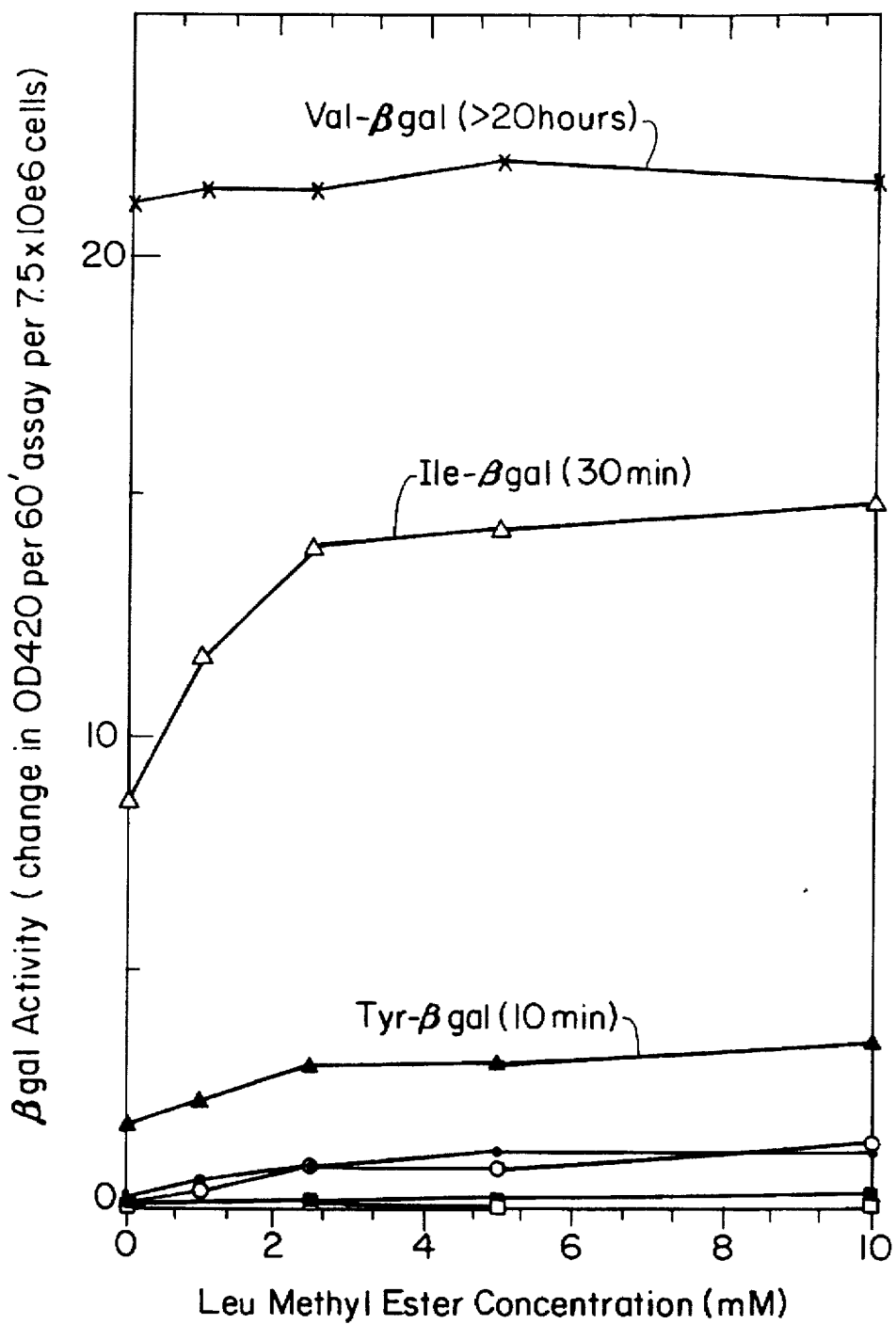

As is also discussed below (Example 5), the metabolic stabilities (in-vivo half-lives) of four additional X-βgal proteins in which the amino terminus is a bulky hydrophobic amino acid residue (phenylalanine-βgal, tryptophan-βgal, tyrosine-βgal and isoleucine-βgal) were increased in the presence of leucine methyl ester (FIGS. 5 and 8). Thus, it has been shown that the N-end rule pathway can be selectively inhibited in living cells by means of amino acid derivatives in which the amino-terminal amino acid residue is the same as or similar to the amino-terminal residue of a protein or proteins whose metabolic stability is to be increased.

In general, regulators which are useful in the present invention are dipeptides, small polypeptides, bulky hydrophobic esters and other carboxyl-terminal derivatives of destabilizing amino acids. For example, any small polypeptide with the appropriate amino-terminal amino acid residue (defined by the N-end rule) can be used as a regulator within the present invention. Examples of carboxyl-terminal locking groups are organic moieties, such as methyl, ethyl, propyl, butyl and isobutyl groups.

The regulator that is useful for the purposes of the present invention should be readily taken up by an intact cell or whole animal, and should accumulate inside the cells to physiologically significant levels. Another useful property of a regulator is its relative resistance to inactivating metabolic transformations, both while enroute into the cell and once inside the cell. An example of a manipulation that increases the resistance of a regulator to inactivation is the use of L-Arg-D-Ala dipeptide instead of L-Arg-L-Ala dipeptide in which both of the constituent amino acid residues have the L configuration. The peptide bond between L-Arg and D-Ala is likely to be more resistant to proteolytic attack inside the cell than the peptide bond in L-Arg-L-Ala, a standard version of this dipeptide. Indeed, as shown in FIG. 9, the use of L-Arg-D-Ala dipeptide results in a stronger metabolic stabilization of Arg-βgal in-vivo than the use of L-Arg-L-Ala dipeptide.

According to the present method, in the case of isolated cells, the regulator can be added directly to the growth medium, or fed under a specified temporal regimen. In the case of whole animals, the regulator can be administered orally, by subcutaneous or other injection, intravenously, parenterally, transdermally, rectally or via an implanted reservoir containing the regulator. The form in which the regulator will be administered (e.g. powder, tablet, capsule, solution, emulsion) will depend on the route by which it is administered. The quantity of the regulator to be administered will be determined on an individual basis, and will be based at least in part on consideration of the individual's size, the severity of the symptoms to be treated and the result sought. Regulators can be included in a composition to be administered by any of these routes. Such a composition may include, in addition to one or more regulators, a carrier (e.g., a polymer that slowly releases a regulator), a physiologically acceptable buffer and an engineered or natural protein, which has a desired function in the body, and whose metabolic stability is to be increased by co-administration of a regulator according to the method of the present invention. In this case, the regulator is designed in such a manner that its amino-terminal amino acid residue is the same as or similar (as defined by the Table) to the amino-terminal (destabilizing) residue of the protein of interest. In this way, the regulator acts to increase the metabolic stability of the protein by interacting with the amino terminus-recognition site of the N-end-recognizing protein, and thereby competitively inhibiting the N-end rule pathway.

Alternatively, a DNA construct which includes a nucleotide sequence encoding the desired amino acid sequence of the regulator can be introduced into cells in which inhibition of the degradation of a specific type or class of proteins is desired. The DNA sequence can be introduced by means of an appropriate vector, e.g. a retroviral vector. All DNA-encoded proteins and peptides start with methionine and, therefore, a construct designed to result in expression of a protein which can be processed by the cell to produce the desired peptide will be used. The DNA constructs to be used are based on the ubiquitin fusion approach described by Bachmair et al., Science 234:179–186 (1986), the contents of which are hereby incorporated by reference. Briefly, the constructs will encode a fusion protein consisting of one ubiquitin moiety followed by an amino acid residue X (where X is any one of the twenty amino acids), and a desired peptide sequence. Expression of this protein in a target cell will result, as shown previously by Bachmair et al., in a rapid deubiquitination of the fusion protein, yielding free ubiquitin and a peptide with the desired amino-terminal residue X. The peptide, when accumulated in the cell to sufficient levels, will specifically inhibit the N-end rule pathway.

In Vivo Inhibitors of the N-end Rule Pathway Show "Zero-Time" Enhancement Effect The susceptibility of a nascent protein to in vivo degradation is, in general, different from the susceptibility of the same protein when mature and fully folded. One reason for this difference stems from the fact that it takes a finite amount of time for a newly formed protein to adopt its mature conformation. During this time interval, which varies from protein to protein, a partially folded protein molecule is more likely to be susceptible to cleavage by in vivo degradation pathways, and in particular by the N-end rule pathway. The latter pathway may preferentially target partially folded proteins for instance because such proteins are likely to be more vulnerable to proteolytic "nibling" at their amino termini. At some point, such "nibling" exposes a destabilizing amino-terminal residue and thereby converts the protein into a substrate for the N-end rule pathway. To distinguish between the kinetically first-order (exponential) degradation of a mature short-lived protein and the non-first order degradation of the same protein when it is newly formed and not yet conformationally mature, the latter type of degradation is called a "pre-exponential" one. Interestingly, the regulator substances of the present invention (the in vivo inhibitors of the N-end rule pathway) inhibit both the pre-exponential and exponential modes of protein degradation in the N-end rule pathway of living cells. As a result, the steady-state levels, of relevant proteins are increased by the regulators in the cell not only through their metabolic stabilization of the mature proteins but also during and immediately after these proteins' synthesis on ribosomes (the so-called "zero-time" effect).

In retrospect, it is remarkable and a priori unexpected that the regulator substances such as, for example, leucine methyl ester, which is readily hydrolyzed in-vivo into methanol and (inactive) free leucine, could be shown to accumulate in living cells to steady state levels sufficient for the specific inhibition of the N-end rule pathway. The results of experiments described in the present invention show that such accumulation does indeed take place, and thus open a new way to selectively inhibit the degradation of specific proteins in intact cells and whole animals.

The invention is illustrated in the following Examples, which are not to be seen as limiting in any way.

EXAMPLE 1

Effect of Leucine Methyl Ester on Yeast Cell Growth

In this and the following examples, reagents, strain and assay methods were described below.

Reagents

Amino acid derivatives (methyl esters and dipeptides) were obtained from BACHEM Bioscience Inc., Philadelphia Pa., and from Sigma Chemical Company. St. Louis Mo.

Strains

*Saccharomyces cerevisiae* cells of the strain BWG1-7a (MATa his4 ade1 ura3 leu2) were transformed with plasmids using conventional techniques (F. Sherman et al. *Methods in Yeast Genetics* Cold Spring Harbor Laboratory. N.Y., 1981). The transformed cells were grown at 30° C. in a medium of 2% galactose, 0.67% Yeast Nitrogen Base without amino acids (Difco), adenine (10 µg/mL), histidine (20 µg/mL) and leucine (60 ug/mL).

Plasmids

Plasmids used were those described by Bachmair t al., *Science* 234:179 (1986), the contents of which are hereby incorporated by reference. Briefly, they encode a fusion protein consisting of one ubiquitin moiety followed by an amino acid residue X (where X is any one of the twenty amino acids), and a β-galactosidase (βgal) protein. Expression of this fusion protein is under the control of the inducible GAL promoter. Once expressed in yeast, the ubiquitin moiety of a fusion protein is rapidly cleaved by an endogenous ubiquitin-specific protease, to yield the residue X at the amino terminus of an X-βgal protein.

Assaying Steady State β-galactosidase Activity

Cells were grown, as described above, to an optical density of 0.2 to 0.5 at $A_{600}$. Amino acid derivatives, described below, were added to the cells from concentrated stocks (buffered with potassium phosphate to pH 7.0), until the desired final concentration was obtained. Incubation was continued at 30° C. Samples (0.5 mL) were withdrawn at indicated times and the cells were collected by centrifugation. Pellets were resuspended in 0.5 mL Z buffer (0.1M sodium phosphate pH 7.0, 10 mM KCl, 1 mM $MgSO_4$, 38 mM 2-mercaptoethanol), $CHCl_3$ (2 drops) and 0.1% SDS (1 drop) were added, and the mixture was vortexed for ten seconds. The assay for βgal enzymatic activity then commenced with the addition of 0.1 mL of a 4 mg/mL o-Nitrophenyl-β-galactopyranoside (ONPG) solution followed by incubation at 30° C. The assay was was terminated by the addition of 0.5 mL of 1M $Na_2Co_3$. Absorbance at 420 nm was measured following clarification of the mixture by centrifugation. In some cases, cells were not pelleted, but 50 uL of culture was added directly to 0.45 mL Z buffer.

Pulse-Chase Experiments In Vivo

Transformed cells were grown as described above, except that methionine (20 ug/mL) was included, to an optical density of about 0.5 at 600 nm. Amino acid derivatives were added and incubation continued for 4 to 5 hours until the optical density was approximately 1.0. Cells from a 10 mL culture were harvested by filtration through the well of a microtiter filtration plate. Subsequently, the cells were washed several times on the filter in the growth medium lacking methionine, and resuspended in 0.4 mL of 1% galactose, 50 mM potassium phosphate buffer (pH 7.4). ($^{35}$S)methionine (100 uCi) was then added for a specified pulse time. The cells were collected by filtration and resuspended in 0.4 mL of the growth medium containing cycloheximide (0.2 mg/mL) and trichodermin (50 ug/mL). Samples (0.1 mL) were withdrawn at indicated times, and added to 0.8 mL of cold Buffer A (50 mM Na-HEPES pH 7.5, 0.15M NaCl, 5 mM EDTA, 1% TRiton X-100) containing leupeptin, pepstatin A, antipain, aprotinin and chymostatin (Sigma), (each at 20 ug/mL) in addition to 0.4 mL of glass beads. The cells were disrupted by vortexing three times for one minute at 4° C. The extracts were centrifuged at 12,000 g for 10 minutes and the radioactivity of acid-insoluble $^{35}$S in the supernatants was determined. Aliquots of the supernatants containing equal amounts of total acid-insoluble $^{35}$S were processed for immunoprecipitation with a monoclonal antibody to βgal. Ascitic fluid containing a molar excess of the antibody (at least ten-fold) was added to each aliquot, with subsequent incubation on ice for 1 to 2 hours. Protein A-Sepharose (Pharmacia) was then added and the suspension was incubated with rocking at 4° C. for 30 minutes and centrifuged at 12,000 g for thirty seconds. The protein A-Sepharose pellets were washed three times in Buffer A containing 0.1% SDS, resuspended in an SDS, dithiothreitol (DTT)-containing electrophoretic sample buffer, heated at 100° C. for 3 minutes, and centrifuged at 12,000 g for 20 seconds. (Laemmli, *Nature* 227, 680 (1970) ). The supernatants were subjected to electrophoresis in a 6% discontinuous polyacrylamide-SDS gel (150 by 150 by 1.5 mm), with subsequent fluorography.

In Vivo Half-life Determination

After fluorography of the pulse-chase gels, the amount of radioactivity in each band was detected by scintillation counting of the respective gel slices. Half-lives were calculated from these values (appropriately adjusted using the value from a blank gel slice) assuming a first-order kinetics of protein breakdown.

Figure 1:
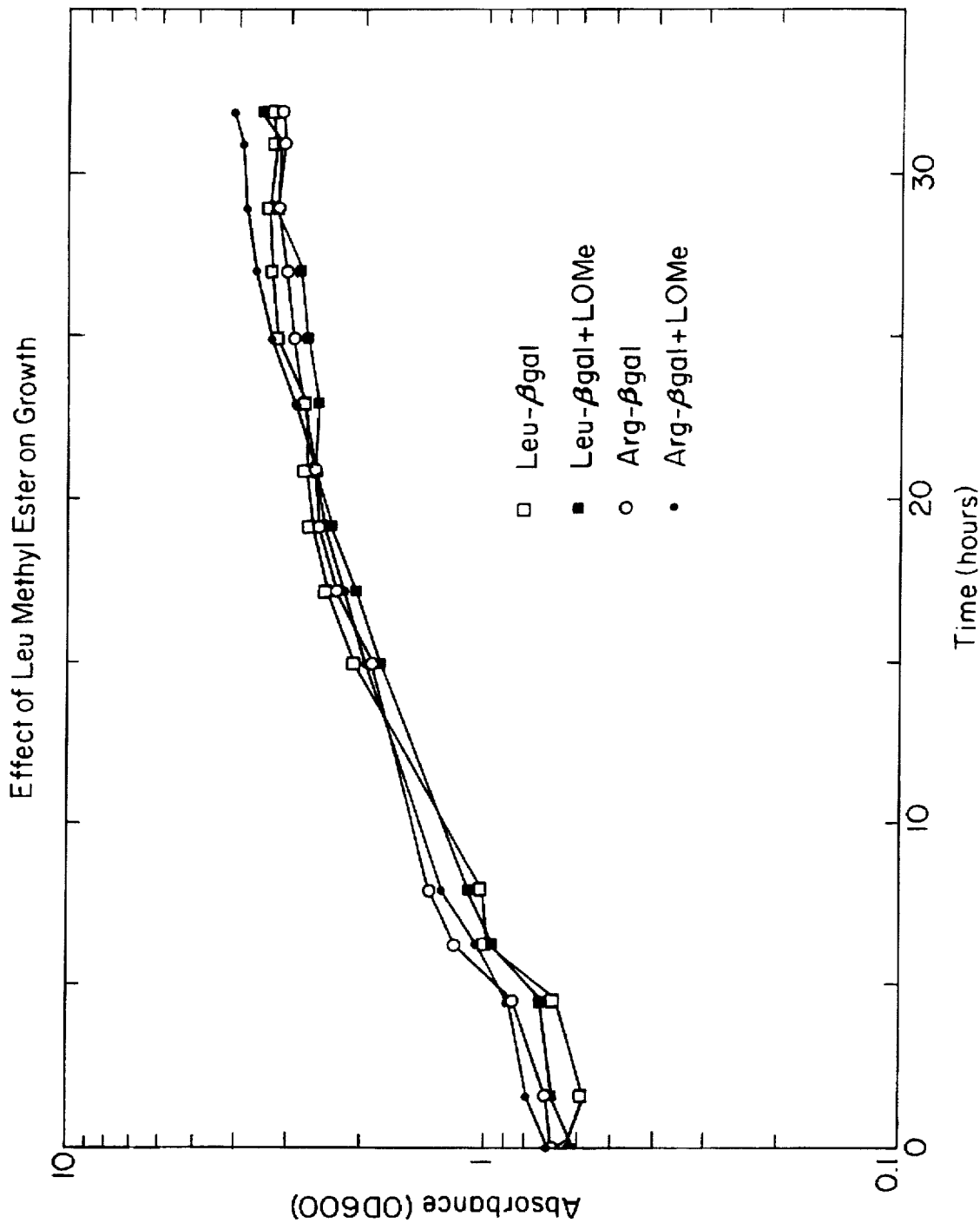
FIG. 1 is a graph showing the effect of adding leucine methyl ester (10 mM final concentration) to exponentially growing yeast (S.cerevisiae) cells harboring a plasmid expressing either Arg-βgal or Leuβgal (specific short-lived proteins that are degraded via the N-end rule pathway). Growth of cells was monitored by measuring optical density at 600 nm.

The effect of 10 mM of leucine methyl ester (Leu methyl ester) on growth of exponentially growing yeast cells harboring a plasmid expressing either arginine-βgal (Arg-βgal, ○, ●) or leucine-βgal (Leu-βgal, □,■), supplemented with nothing (○,■) or with Leu methyl ester to a 10 mM final concentration (■,●), was assessed. Results are represented in FIG. 1. Growth under each of these conditions was monitored by optical density at 600 nm. As shown in FIG. 1, the Leu methyl ester had no adverse effects on cell growth. It should also be noted that no adverse effect on yeast cell growth by the dipeptides Arg-Ala and Ala-Arg (used in Example 4), Trp-Ala, or Ala-Trp (used in Example 7) was evident over the time periods used (data not shown).

EXAMPLE 2

Effect of Leucine Methyl Ester at Varying Initial Cell Density

Yeast cells harboring a plasmid expressing either Arg-βgal (○,●) or Leu-βgal (□, ■) were supplemented with Leu methyl ester to 10 mM final (●,■) at varying initial $OD_{600}$, and assayed for βgal activity after 3 hours incubation. Control cultures (○, □) received no methyl ester.

Results, presented in FIG. 2, showed that Leu methyl ester (Leu-OMe) specifically increases the steady state activity (amount) of Leu-βgal (a bulky hydrophobic amino terminus) but does not increase the amount of Arg-βal (a basic amino terminus). The results of FIG. 2 also show that the effect is more pronounced in exponentially growing cells (i.e., at lower OD's). Therefore, subsequent work used cultures at $OD_{600}$ of approximately 0.5–1.0.

EXAMPLE 3

Time Course Study of Effect of 10 mM Leucine Methyl Ester on Steady State Levels Of Leucine-βal In Vivo Exponentially growing yeast cells harboring a plasmid expressing Leu- βal were supplemented with Leu methyl ester to the 10 mM final concentration (zero time) and assayed for βgal activity over a 7 hour time course (■). A control culture (□) received no methyl ester.

Figure 3:
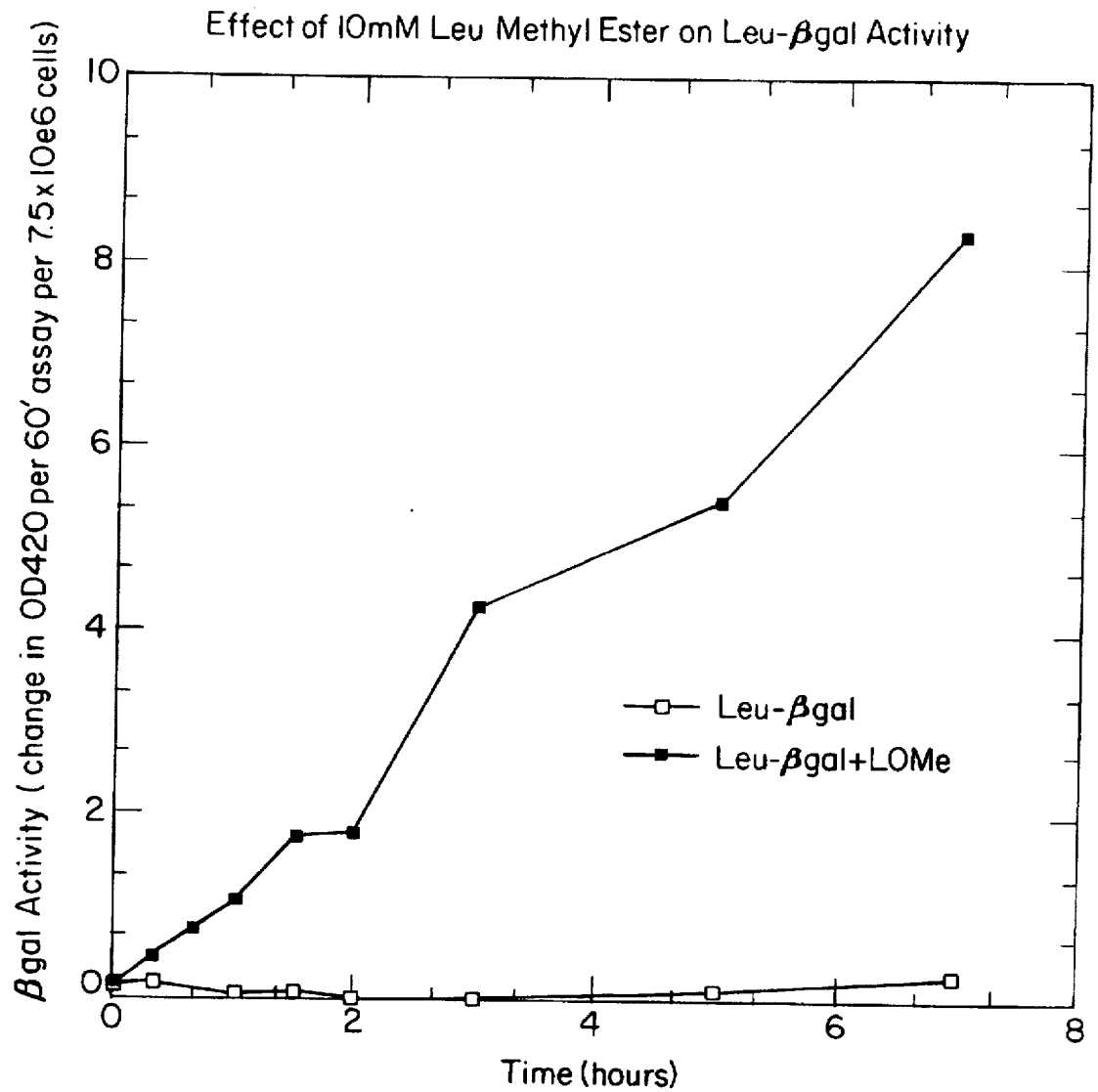
FIG. 3 is a graphic representation of the effect of Leu methyl ester over a seven hour time period on steady state levels of Leu-βgal. Leu methyl ester (10 final concentration at zero time) was added to exponentially growing yeast cells harboring a plasmid expressing Leu-βgal.

Results are represented in FIG. 3 and showed that the magnitude of the effect of Leu-OMe on Leu-βgal levels increases linearly with time (at least for the first 7 hours). The slope of the line of best fit yields an 11-fold increase in βgal level per hour when the Leu-OMe concentration was 10 mM (when compared with control levels).

EXAMPLE 4

Time Course Study of Effect of Arginine-Containing Dipeptides on Steady State Arg-βgal Levels In Vivo Exponentially growing yeast cells harboring a plasmid expressing Arg-βgal were supplemented with: sample buffer (□) 10 mM (final) L-arginine-L-alanine (L-Arg-L-Ala,■), and 10 mM (final) L-alanine-L-arginine (L-Ala-L-Arg,○). βgal activity was assayed over a 7 hour time course and plotted as a function of time.

Figure 4:
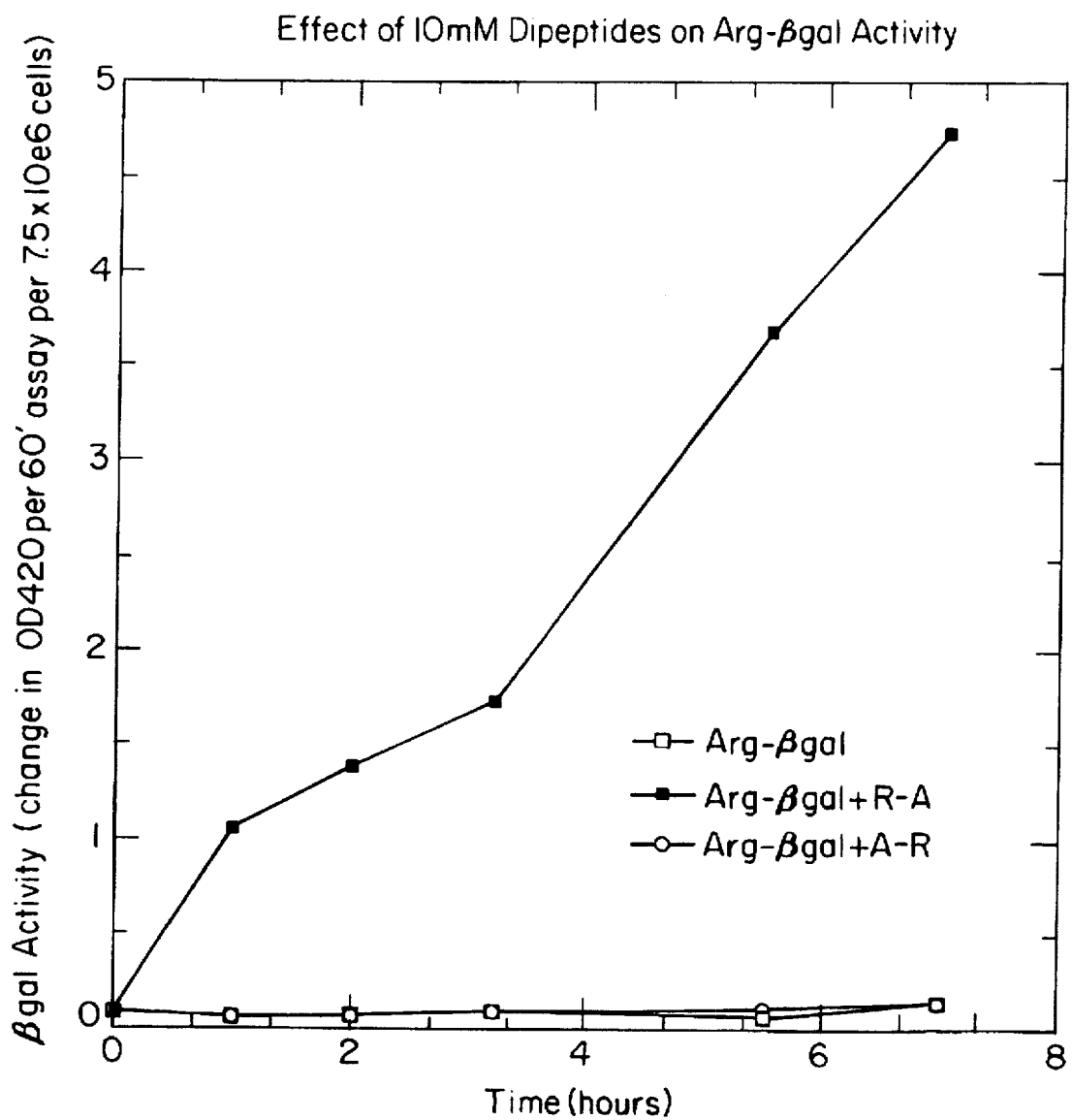
FIG. 4 is a graphic representation of the effect of dipeptides containing the amino-terminal Arg residue on steady state levels of Arg-βgal in yeast cell over a seven hour time period. Arg-containing dipeptides were added to exponentially growing yeast cells harboring a plasmid expressing Argβgal.

Results are shown in FIG. 4. The magnitude of the effect of the dipeptide L-Arg-L-Ala on Leu-βgal levels increases linearly with time. The slope of the line of best fit yields an 8.5-fold increase in βgal level per hour when the L-Arg-L-Ala concentration was 10 mM (compared with control levels). L-Ala-L-Arg had no effect. This indicates that the order of amino acids in the dipeptide is crucial for its inhibiting activity. Specifically, Arg must be at the amino terminus of the dipeptide to have an effect.

EXAMPLE 5

Leucine Methyl Ester Increases In Vivo Steady State Levels of All X-βgal Test Proteins with Bulky Hydrophobic Amino-terminal Residues Exponentially growing yeast cells harboring plasmids expressing phenylalanine-βgal (Phe-βgal,■), leucine-βgal (Leu-βgal,○), tryptophan-βgal (Trp-βgal,●), tyrosine-βgal (Tyr-βgal,▲) and isoleucine-βgal (Ile-βgal,♦) were supplemented with Leu methyl ester at concentrations ranging from 0 to 10 mM, incubated for 1 hour, and assayed for βgal activity. As controls, cells harboring Arg-βgal (□) and Val-βgal (*) plasmids were identically treated. Half-lives of the X-βgal proteins (as determined by Bachmair et al., Science 234:179–186 (1986)) are given in parentheses. Results are represented in FIG. 5, in which the data from experiments involving the relatively short-lived X-βgals are plotted for clarity at a larger scale (left panel).

Results show that variation in the concentrations of the various X-βgal's in the absence of Leu-OMe is due to the varying half-lives of X-βgal's (see Bachmair et al., Science 234:179–186 (1986)). The longer the half-life, the higher the zero time activity observed. Results also show that the levels of all 5 X-βgal proteins with bulky hydrophobic amino termini are increased in the presence of Leu-OMe over the amount of each with no OMe added. Generally, this effect reaches saturation at approximately 5–10 mM Leu-OMe. No effect was seen with Arg-βal, which has a basic amino terminus and a half-life of approximately 2 minutes, or on Val-βal, which is long-lived (half life >20 hours).

EXAMPLE 6

Stabilization of Leucine-βgal In vivo by Leucine Methyl Ester

A pulse-chase experiment (5 minute pulse) was carried out with cells expressing Val-βgal (A), or Leu-βgal in the presence (B) or absence (C) of a 3 hour incubation with 10 mM Leu methyl ester. Timepoints: 0 min (lane 1); 10 min (lane 2); and 30 min (lane 3). Bands are labelled: βgal (β-galactosidase); 90 kD (a cleavage product of βgal; note its absence from the lanes with metabolically stable Val-βgal lanes); X (an unrelated protein species crossreacting with the monoclonal antibody to βgal); and S (a βgal cleavage product apparently specific for metabolically stable X-βgal; species).

Figure 6:
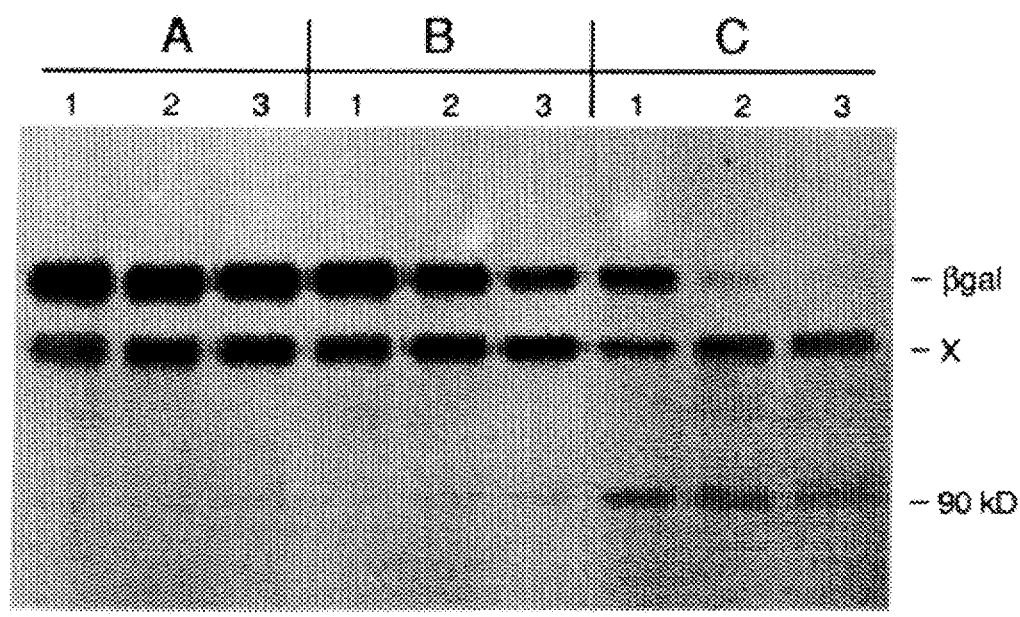
FIG. 6 is a photograph showing the metabolic stabilization of Leu-βgal by Leu methyl ester in growing yeast cells. The photograph depicts the gel resulting from a pulse-chase electrophoretic experiment (5 minute pulse) with cells expressing Val-βgal (A), or Leu-βgal in the presence (B) or absence (C) of a 3 hour preincubation with 10 mM Leu methyl ester. The time-points are 0 minutes for lane 1, 10 minutes for lane 2, and 30 minutes for lane 3.

Results are represented in FIG. 6. They show that the half-life of Leu-βgal is increased in the presence of Leu-OMe. Calculated half-lives (from 0 to 10 minute time point values): minus OMe=4 minutes, plus OMe=12 minutes: i.e., a 3-fold increase. They also show that there is a "zero-time" boost in the amount of Leu=βgal in the presence of OMe (compareβgal band, lane 1 in B and C). There is a 1.9-fold increase in the amount of protein in this band. Note also the much diminished 90 kD βgal cleavage product in the presence of OMe, indicating that less βgal is being broken down by this proteolytic route.

EXAMPLE 7

Stabilization of Leucine-βgal In Vivo by L-Trp-L-Ala, but Not by L-Ala-L-Trp

A pulse-chase experiment (5 minute pulse) was carried out with cells expressing Val-βgal (A), Leu-βgal (B), Leu-βgal plus 10 mM L-Ala-L-Trp (C), and Leu-βgal plus 10 mM L-Trp-L-Ala (D). Incubation with each dipeptide was carried out for 4 hours. Timepoints: 0 min (lane 1); 10 min (lane 2); and 30 min (lane 3). See legend to FIG. 6 for band designations.

Results are presented in FIG. 7. They show that the half-life of Leu-βgal is lengthened in the presence of L-Trp-L-Ala (D), but not in the presence of L-Ala-L-Trp (C). Note that the βgal cleavage product "S" is observed only in the lanes of metabolically stable Val-βgal (see discussion of FIG. 8).

EXAMPLE 8

Stabilization of Tyr-βgal In Vivo by Leu Methyl Ester

A pulse-chase experiment (3 minute pulse) was carried out with cells expressing Tyr-βgal in the absence (A) or presence (B) of a 4 hour incubation with 10 mM Leu methyl ester. Timepoints: 0 min (lane 1); 10 min (lane 2); 30 min (lane 3); and 60 min (lane 4). See legend to FIG. 6 for band designations. Results are shown in FIG. 8. They show that the in-vivo half-life of Tyr-βal is increased in the presence of Leu-OMe. Calculated half-lives: minus OMe=7.5 minutes, plus OMe—36.4 minutes: i.e., a 4.8-fold increase.

Note also the zero-time boost again; there is a 3.3-fold increase in the amount of protein in the presence of OMe. Tyr-βgal is a better demonstrator of this effect, as the pulse time used (3 min) is much less than the half-life of Tyr-βgal (7.5 min), and hence any increase in the "zero-time" amount is clearly not due to accumulation of βgal solely because of the increase in its half-life. In the case of Leu-βgal (FIG. 6), where the pulse is just longer than the half-life (5 vs. 4 minutes), the zero time boost could be due in part to the accumulation of βgal during the pulse because the OMe is extending the half-life of βgal. Note the presence of the βgal breakdown product "S" in panel B, which is normally only seen with metabolically stable X-βgals. Thus, in the presence of Leu-OMe, the cell's degradative mechanisms are treating Tyr-βal as a metabolically "stable" βgal species.

EXAMPLE 9

Effect of Stereoconfiguration of the Peptide Bond in the Arg-Ala_Dipeptide on Its Ability to Stabilize Arg-βgal In Vivo Cells expressing Arg-βgal and Val-βal were incubated for 2 hours in the presence of one of three dipeptides: L-Arg-D-Ala, L-Arg-L-Ala or L-Ala-L-Arg. βgal activity was then determined as described above and plotted relative to the activity of an untreated control ("con"). Actual βgal activity is given above each column. Stereoconfigurations are of the "L" form, unless otherwise noted.

Results are represented in FIG. 9. They show that L-Arg-D-Ala is a much better in vivo metabolic stabilizer of Arg-βgal than is L-Arg-L-Ala, while L-Ala-L-Arg has no effect. Presumably, the "D" stereoconfiguration of the peptide bond is more resistant to cleavage in-vivo, which results in a lower rate of inactivation of the dipeptide as an in vivo inhibitor of the N-end rule pathway.

We claim:

1. A method for increasing the half-life of a Type I non-compartmentalized intracellular protein in a eukaryotic cell, the method comprising contacting the cell with a dipeptide having an N-terminal amino acid residue selected from the group consisting of Arg, Lys and His.

2. A method of claim 1 wherein the cell is a yeast cell.

3. A method for increasing the half-life of a Type II non-compartmentalized intracellular protein in a eukaryotic cell, the method comprising contacting the cell with a dipeptide having an N-terminal amino acid residue selected from the group consisting of Phe, Leu, Trp, Tyr and Ile.

4. A method of claim 3 wherein the cell is a yeast cell.

5. A method for increasing the half-life of a Type III non-compartmentalized intracellular protein in a eukaryotic cell, the method comprising contacting the cell with a dipeptide having an N-terminal amino acid residue selected from the group consisting of Ala, Ser and Thr.

6. A method of claim 5 wherein the cell is a yeast cell.

* * * * *